United States Patent [19]

Forberg

[11] 4,037,597

[45] July 26, 1977

[54] DRIP CHAMBER FOR INFUSION AND TRANSFUSION APPARATUS FORMED OF SEVERAL PARTS

[75] Inventor: Hans-Jürgen Forberg, Lensahn, Holst, Germany

[73] Assignee: Firma Transcodan Sven Husted-Anderson, Germany

[21] Appl. No.: 592,881

[22] Filed: July 3, 1975

[30] Foreign Application Priority Data

July 3, 1974 Germany .............................. 2331946
Mar. 5, 1975 Germany .............................. 2509484

[51] Int. Cl.² .............................................. A61M 5/16
[52] U.S. Cl. .................................. 128/214 C; 215/321
[58] Field of Search ............ 128/214 R, 214 C, 214.2, 128/221, 275; 215/317, 320, 321; 220/306, 354, 355

[56] References Cited

U.S. PATENT DOCUMENTS

| | | | |
|---|---|---|---|
| 828,936 | 8/1906 | Hicks | 215/321 |
| 2,681,654 | 6/1954 | Ryan et al. | 128/214 C |
| 3,021,841 | 2/1962 | Burke | 128/214 C |
| 3,316,908 | 5/1967 | Burke | 128/214 C |
| 3,458,079 | 7/1969 | Gasbarra | 150/.5 X |
| 3,556,338 | 1/1971 | Wilkinson et al. | 215/320 X |
| 3,892,327 | 7/1975 | Leitz | 215/321 X |

*Primary Examiner*—Dalton L. Truluck
*Attorney, Agent, or Firm*—McGlew and Tuttle

[57] ABSTRACT

The drip chamber comprises a first part formed with a feed pipe or liquid duct terminating in a grooved tubular piercing needle at one end of the first part, the other end of the first part terminating in a bell-shaped cover. A second part of the drip chamber is constructed by a liquid chamber having one end engaged with the bell-shaped cover and the opposite end terminating in a hose or conduit. The bell and the liquid chamber are interconnected, at their junction with each other, by interengageable clampingly interlocking components forming, when interengaged, a labyrinth packing providing a liquid tight seal at the junction. The two parts are interconnected by a snap interfit of the interlocking components.

13 Claims, 5 Drawing Figures

DRIP CHAMBER FOR INFUSION AND TRANSFUSION APPARATUS FORMED OF SEVERAL PARTS

FIELD AND BACKGROUND OF THE INVENTION

This invention is directed to drip chambers for infusion and transfusion apparatus, in which the drip chambers comprise several rigidly interconnected parts.

Such drip chambers generally are formed of at least two-parts, the so-called piercing mandrel or grooved tubular piercing needle and the housing of the liquid chamber. The parts can consist of different material, but generally are made of a plastic composition material, and the parts are rigidly connected with each other in various ways at their junctions. The manufacture of the known joints presents difficulties.

Thus, not all materials of which the apparatus is made are suitable for adhesive joints. If the parts are to be cemented with each other at their junctions, one is confined to certain materials which are diadvantageous, however, for the manufacture and the use of the parts of the apparatus for other reasons.

The same holds generally true for welded joints, in that these too permit the selection of only a few materials. Additionally, with welded joints, there is a risk of lack of tightness in the production of the joint.

It is also known to spray the junction between the parts with plastic, but this method is very complicated and consequently expensive. Also, with this method, there is the risk of lack of tightness of the junctions in mass production.

Summarizing, it can be said that known types of joints for drip chambers for infusion and transfusion apparatus are either expensive or have only a limited application, or that there is a risk of the junction between the parts not being tight and thereby not forming a liquid tight seal between the parts.

SUMMARY OF THE INVENTION

The invention is directed to solving the problem of providing a joint, between the parts, which is simple in design and manufacture and which is suitable for all materials used in the manufacture of the parts of a drip chamber for infusion and transfusion apparatus, so that the parts furthermore can consist of different materials, if necessary. In particular, the type of joint should not limit the selection of the materials, and the joint should be inexpensive to produce in mass production and should avoid the risk of untightness at the junction between the parts.

The joint according to the present invention is simple in design, inexpensive to produce, easy to assembly, not limited to certain materials, and provides a liquid tight seal for a long period of time. Even if the packing elements show slight deviations from the standard dimensions, the parts can be easily pressed together.

In a simple embodiment of the invention, at least one packing component is provided with two juxtaposed packing straps, and the other packing component is provided with at least one packing strap engaging the groove between these two packing straps. A very tight joint is obtained if both parts are provided with at least two packing straps in this manner, and which form a double tongue and groove joint.

In order to make the joint secure, the parts to be connected with each other can be provided with interlocking components of a snap joint. Such a snap joint is inexpensive to produce, simple to mount, and independent of the particular materials. Thus, minor error possibilities do not affect the mounting and the right fit is simple to control. During assembly, the end position is controlled by locking the snap joint, and the tight joint can not open accidentally. The tight joint prevents the risk that the two parts will separate during use of the trip chamber, for example, in the compression of the drip chamber to obtain a pump effect, or that the joint can leak.

Locking by a snap joint can be obtained, in the case of plastic parts, by undercutting packing components, for example, of the labyrinth packing. The undercut is so designed that the parts can be removed from an injection-molding tool.

In a simple solution in accordance with the invention, the packing strap of one part is provided with a flange behind which there extend hook-shaped projections arranged on the other part in the interconnected condition of the two parts. In this way, so-called "snap catches" are formed, and replace the undercut, and these snap catches are elastic. An advantageous embodiment consists in that the outer surface of the flange is inclined or bevelled, as viewed in profile, over its entire surface or partly in the direction to the other part, to form sliding surfaces.

The components used for the snap joint, like the hook-shaped projections, can be arranged on a circumferential strap. The hook-shaped projections also can be provided on their outer surfaces with inclined or bevelled sliding surfaces to facilitate the locking of the snap joint.

Due to its design, the labyrinth packing embodying the invention is liquid tight. In order to further assure a liquid tight seal, a packing ring can be provided between the components forming the labyrinth packing.

In a further development of the invention, the edge of one part of the drip chamber is provided with a circular groove and the edge of the other part with a circular socket engaging within the groove, and which is provided with fins or ribs on at least one surface. These fins or ribs can act in various ways. Thus, they can be packing fins.

If the fins are arranged on the outer surface of the socket, they can have an outside diameter which is slightly greater than the inside diameter of the outer wall of the groove of the other part of the chamber. If the fins are arranged on the inner surface of the socket, they can have an inner diameter which is slightly smaller than the outer diameter of the inner wall of the annular groove on other part. In both cases the fins form, so to speak, circumferential joints when the two parts are assembled with each other.

However, the fins can also act as clamping fins, since they increase considerably the friction between the fitted parts in the above described case. Both parts are, in this case, connected with each other solely by the clamping action. For the assembly of the drip chamber, it is only necessary to press the two parts together and, even if the parts of the packing differ slightly from the standard dimensions, the two parts can be joined with each other.

A simple embodiment of this development of the invention consists in that recesses are provided between the clamping fins This embodiment has the advantage that the clamping fins have a larger outside diameter and a smaller inside diameter, respectively, than if such recesses were not provided. The fins can yield sufficiently during the assembly of the parts, due to the recesses provided between the fins, so that the parts can be fitted together. On the other hand, the packing or clamping action is increased.

In accordance with another embodiment of this development, the fins, the recesses, or both can be annular.

A very simple embodiment of the drip chamber embodying the invention is obtained if the lower part of the drip chamber is provided with the socket and the upper part with the groove. This embodiment is particularly simple if the upper edge of the wall of the drip chamber forms, at the same time, the socket, in which case a particularly simple form of the individual parts is obtained.

The parts to be joined together with each other furthermore can be provided with interlocking components of a snap joint or similar joint, which insures the security of the connection between the parts.

In accordance with another embodiment of the invention, the socket arranged in one part can be provided with an offset or indentation, or the like, as viewed in profile, which is engaged by a projection arranged on the other part in the connected condition of the two parts. Also, a packing ring could be arranged between the individual parts.

An object of the invention is to provide an improved junction between the several separate parts of a drip chamber for infusion and transfusion apparatus.

Another object of the invention is to provide such a junction comprising interengageable clampingly interlocking components on the two parts forming, when interengaged, a labyrinth packing.

A further object of the invention is to provide an improved drip chamber for infusion and transfusion apparatus in which the parts are interconnected in a manner such that liquid tight seals are formed at the junctions between the parts.

For an understanding of the principles of the invention, reference is made to the following description of typical embodiments thereof as illustrated in the accompanying drawings.

DESCRIPTION OF THE PREFERRED EMBODIMENTS

Figure 1:
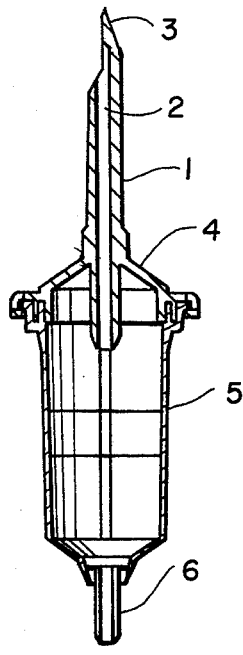
FIG. 1 is a longitudinal sectional view of a drip chamber, for infusion and transfusion apparatus, embodying the invention.
Figure 3:
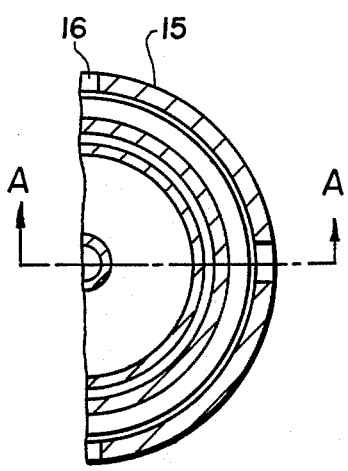
FIG. 3 is a sectional view taken on the line B-B of FIG. 2.
Figure 2:
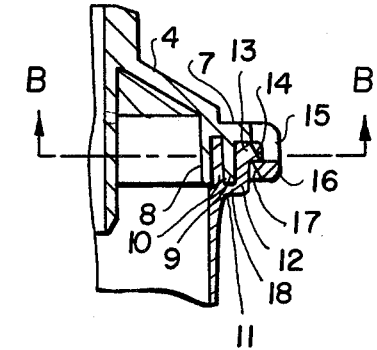
FIG. 2 is a sectional view, to an enlarged scale, of a detail in FIG. 1, the section being taken on the line A—A of FIG. 3.

Referring first to the embodiment of the invention shown in FIGS. 1, 2 and 3, the drip chamber embodying the invention consists of an upper part 1 having a feed pipe or liquid duct 2 which terminates in a grooved tubular piercing needle 3. The upper part 1 can be provided with an air duct, which has not been shown. The bottom end of upper part 1 has a bell-shaped cover 4 through which liquid duct 2 extends.

The lower part of the drip chamber is constituted by the liquid chamber 5, whose lower end has connected thereto the hose 6.

In accordance with the invention, the end face 7 of bell-shaped cover 4 is provided with two packing strips 8 and 9, as best seen in FIGS. 2 and 3. The space between these packing strips is engaged by a packing strip 10 of housing 5, whose front edge 11 is provided with another packing strip 12 whose upper edge is provided with an outwardly protruding flange 13. Flange 13 has a bevelled surface 14.

Bell-shaped cover 4 is provided, at angularly spaced locations, with inwardly protruding hook-shaped projections 16 whose radially inner surfaces are bevelled at 17. In the space defined by straps 8 and 9 and that defined by straps 10 and 12, there can be arranged a packing ring 18.

In the embodiment shown in FIGS. 1, 2 and 3, four hook-shaped projections 16 are provided on the strap 15, and these hooks can easily be removed from the mold since the material of upper part 1 consists of plastic and is elastic.

The two parts of the drip chamber can consist of different materials, and are joined with each other by pressing the two parts firmly against each other so that opening of the drip chamber, and separation of the parts from each other during use, is not possible. Several hook-shaped projections, serving as a mounting support, can be provided. In the connected position shown in FIGS. 1 and 2, hook-shaped projections 16 extend behind flange 13 and assure a firm interconnection of parts 1 and 2.

Figure 4:
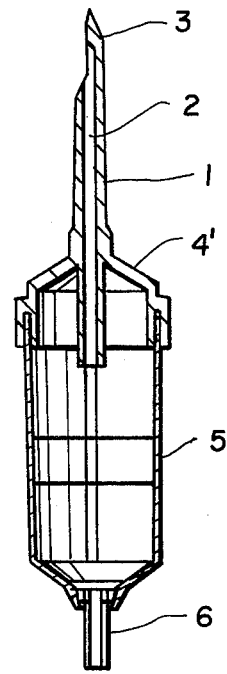
FIG. 4 is a view, similar to FIG. 1, of another embodiment of a drip chamber in accordance with the invention.
Figure 5:
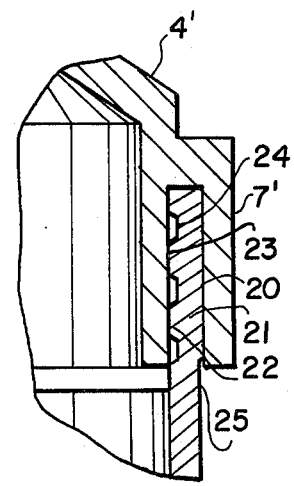
FIG. 5 is a sectional view to an enlarged scale, of the detail of the housing seal shown in FIG. 4.

In the embodiment of the invention shown in FIGS. 4 and 5, parts identical or substantially identical with those shown in the embodiment of the invention of FIGS. 1, 2 and 3 have been given the same reference characters. Furthermore, parts identical with those of FIGS. 1, 2 and 3 will not be described in detail.

Referring to FIGS. 4 and 5, end face 7' of bell-shaped cover 4' is provided with an annular groove 20 into which the edge 21 of the wall of liquid chamber 5 can be directly inserted. In this embodiment, the socket of one part of the drip chamber, which serves as a packing, is thus formed directly by the edge 21 of liquid chamber 5.

Edge 21 is formed or otherwise provided with inwardly directed fins or ribs 22 which, in the illustrated embodiment, are annular fins or ribs. The inner diameter of these fins or ribs 22 is slightly smaller than the outer diameter of the inner wall 23 of annular groove 20. Between fins and ribs 22, there are provided recesses 24 which are also in the form of annular grooves.

When the parts are joined together, the outer edges of the fins or ribs 22 can therefore yield slightly, so that the fins are put under initial stress. Accordingly, a satisfactory liquid-tight seal is achieved by fins or ribs 22 bearing, under initial stress, on wall 23. On the other hand, an increased frictional contact is attained by this initial stress between the two parts, so that the parts 1 through 4', on the one hand, and part 5, on the other hand, are held together by a clamping action.

Fins or ribs 22, and the interposed recesses 24, can also have a different form, so that manufacture is simplified as far as possible. Edge 21 can be provided on its outer surface with an indentation, offset, undercut, or the like 25 into which material is pressed from the edge of end face 7' of bell-shaped cover 4' so that a flange is formed, so to speak, on part 7'. Instead of the above described joint, there can be used also any other joint, such as a locking joint, a snap joint, and the like.

While specific embodiments of the invention have been shown and described in detail to illustrate the application of the principles of the invention, it will be understood that the invention may be embodied otherwise without departing from such principles.

What is claimed is:

1. In a drip chamber for infusion and transfusion apparatus formed of separate parts joined together at junctions, with one end part having a liquid duct communicating therewith and terminating in a piercing needle and another end part having a hose communicating therewith, the improvement comprising, in combination, interengageable clampingly interlocking packing components, on the adjacent edges of the parts at said junctions, telescopingly interengageably by movement of the adjacent ends toward each other and forming, when interengaged, a labyrinth packing including a plurality of sealingly interengaged sealing surfaces, whereby liquid-tight seals are formed at said junctions; the two parts joined together at a junction being provided with interlocking components which are hooked over each other, the interlocking components having bevelled surfaces which interengage with each other during assembly of the two parts.

2. In a drip chamber for infusion and transfusion apparatus formed of separate parts joined together at junctions, with one end part having a liquid duct communicating therewith and terminating in a piercing needle and another end part having a hose communicating therewith, the improvement comprising, in combination, interengageable clampingly interlocking packing components, on the adjacent edges of the parts at said junctions, telescopingly interengageably by movement of the adjacent ends toward each other and forming, when interengaged, a labyrinth packing including a plurality of sealingly interengaged sealing surfaces, whereby liquid-tight seals are formed at said junctions; at least one packing component comprising two spaced substantially parallel packing straps on one drip chamber part; the packing component on the other drip chamber part comprising at least one packing strap engaging a groove formed between said two packing straps; the packing strap on one of the two parts joined at a junction being formed with a flange and hook-shaped projections provided on the other part engageable behind said flange in the connected position of the two parts.

3. In a drip chamber for infusion and transfusion apparatus, the improvement claimed in claim 2, in which said flange, in cross section, is bevelled over at least part of its periphery in the direction of said other part so as to form a sliding surface.

4. In a drip chamber for infusion and transfusion apparatus, the improvement claimed in claim 2, in which said hook-shaped projections are arranged on a circumferentially extending strap.

5. In a drip chamber for infusion and transfusion apparatus, the improvement claimed in claim 4, in which the free edges of said hook-shaped projections are bevelled to form inclined sliding surfaces.

6. In a drip chamber for infusion and transfusion apparatus formed of separate parts joined together at junctions, with one end part having a liquid duct communicating therewith and terminating in a piercing needle and another end part having a hose communicating therewith, the improvement comprising, in combination, interengageable clampingly interlocking packing components, on the adjacent edges of the parts at said junctions, telescopingly interengageably by movement of the adjacent ends toward each other and forming, when interengaged, a labyrinth packing including a plurality of sealingly interengaged sealing surfaces, whereby liquid-tight seals are formed at said junctions; the edge of one part at a junction being formed with an annular groove, and the edge of the other part at the junction being formed with an annular socket wall engaging in the groove and formed with rib-shaped fins on at least one surface.

7. In a drip chamber for infusion and transfusion apparatus, the improvement claimed in claim 6, in which recesses are provided between adjacent rib-shaped fins.

8. In a drip chamber for infusion and transfusion apparatus, the improvement claimed in claim 7, in which said fins and recesses are annular.

9. In a drip chamber for infusion and transfusion apparatus, the improvement claimed in claim 6, in which said drip chamber comprises an upper part having an upper end provided with a grooved tubular piercing needle and a lower end formed with a bell-shaped cover, and a lower part constituting a liquid chamber; said bell-shaped cover being formed with said groove and said drip chamber being formed with said socket having said socket wall.

10. In a drip chamber for infusion and transfusion apparatus, the improvement claimed in claim 9, in which said socket wall is formed by the upper edge of the peripheral wall of said drip chamber.

11. In a drip chamber for infusion and transfusion, the improvement claimed in claim 6, in which the assembled parts are provided with interlocking elements of a snap-joint type.

12. In a drip chamber for infusion and transfusion apparatus, the improvement claimed in claim 6, in which said socket wall is formed with an indentation, as viewed in profile, and said groove is formed with a projection engageable in said indentation.

13. In a drip chamber for infusion and transfusion apparatus, the improvement claimed in claim 12, including a packing ring interposed between said groove and said socket wall.

* * * * *